US008357365B2

(12) United States Patent
Kim

(10) Patent No.: US 8,357,365 B2
(45) Date of Patent: *Jan. 22, 2013

(54) GRANULYSIN PEPTIDES AND METHODS OF USE THEREOF

(75) Inventor: Jenny J. Kim, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 941 days.

This patent is subject to a terminal disclaimer.

(21) Appl. No.: 11/815,650

(22) PCT Filed: Feb. 14, 2006

(86) PCT No.: PCT/US2006/005306
§ 371 (c)(1),
(2), (4) Date: Dec. 18, 2008

(87) PCT Pub. No.: WO2006/088945
PCT Pub. Date: Aug. 24, 2006

(65) Prior Publication Data
US 2009/0117093 A1 May 7, 2009

Related U.S. Application Data

(60) Provisional application No. 60/653,232, filed on Feb. 14, 2005.

(51) Int. Cl.
*C12P 21/04* (2006.01)
*C12N 1/12* (2006.01)

(52) U.S. Cl. .................. 424/94.64; 424/9.411; 435/71.3; 435/252.1

(58) Field of Classification Search .......................... None
See application file for complete search history.

(56) References Cited

U.S. PATENT DOCUMENTS

| 4,994,369 A | 2/1991 | Krensky et al. |
| 6,485,928 B2 | 11/2002 | Stenger et al. |
| 6,673,908 B1 | 1/2004 | Stanton, Jr. |
| 6,713,078 B2 | 3/2004 | Lehrer et al. |
| 7,314,858 B2 | 1/2008 | Lehrer et al. |
| 7,459,439 B2 | 12/2008 | Modlin et al. |

FOREIGN PATENT DOCUMENTS

WO 2005/090385 9/2005

OTHER PUBLICATIONS

Technical Information, N-terminal acylation and N-terminal amidation of peptides, Thermo Electron Corp. 2004.*
Raychaudhuri et al Lesional T cells and dermal dendrocytes in psoriasis plaque express increased levels of granulysin. Journal of the American Academy of Dermatology vol. 51, Issue 6, Dec. 2004, pp. 1006-1008.*
Anderson; et al., Granulysin Crystal Structure and a Stucture-derived Lytic Mechanism, J. Mol. Biol. (2003), 325 (2):355-65.
Ernst; et al., Granulysin, a T Cell Product, Kills Bacteria by Altering Membrane Permeability, The Journal of Immunology (2000), 165:7102-7108.
Jongstra; et al., "The Isolation and Sequence of a Novel Gene From a Human Functional T Cell Line", J. Exp. Med. (1987), 165:601-614.
McInturff; et al., "Granulysin-Derived Peptides Demostrate Antimicrobial and Anti-Inflammatory Effects Against *Propionibacterium acnes*", The Journal of Investigative Dermatology (2005), 125:256-263.
Stenger; et al., "An Antimicrobial Activity of Cytolytic T Cells Mediated by Granulysin", Science (1998), 282 (5386):121-5.
Wang; et al., "Bactericidal and Tumoricidal Activities of Synthetic Peptides Derived from Granulysin", The Journal of Immunology (2000), 165(3):1486-90.

* cited by examiner

*Primary Examiner* — Kagnew H Gebreyesus
(74) *Attorney, Agent, or Firm* — Bozicevic, Field & Francis LLP; Pamela J. Sherwood

(57) ABSTRACT

Granulysin peptides are small antimicrobial agents with potent activity. A pharmaceutical composition comprising granulysin peptides as an active agent is administered therapeutically to a patient for exfoliation, e.g. for the treatment of skin lesions.

5 Claims, 6 Drawing Sheets

SEQUENCE LISTING

<160> NUMBER OF SEQ ID NOS: 27

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Thr Arg Val Cys Arg Thr Gly Arg Ser Arg Trp Arg Asp Val Cys Arg
1               5                   10                  15

Asn Phe Met Arg
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide

<400> SEQUENCE: 2

Ala Ala Thr Arg Val Ser Arg Thr Gly Arg Ser Arg Trp Arg Asp Trp
1               5                   10                  15

Ser Arg Asn Phe Met Arg
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Glu Arg Val Ser Arg Thr Gly Arg Ser Arg Trp Arg Asp Trp Ser Arg
1               5                   10                  15

Asn Phe Met Arg Arg Arg
            20

<210> SEQ ID NO 4
<211> LENGTH: 22
<212> TYPE: PRT
<213> ORGANISM: Artificial Sequence
<220> FEATURE:
<223> OTHER INFORMATION: Synthetic peptide

<400> SEQUENCE: 4

Arg Arg Val Ser Arg Thr Gly Arg Ser Arg Trp Arg Asp Trp Ser Arg
1               5                   10                  15

Asn Phe Met Arg Arg Arg
            20

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide

<400> SEQUENCE: 5

Arg Ser Arg Trp Arg Asp Val Ala Arg Asn Phe Met Arg
1               5                   10

```
<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

Arg Ser Arg Trp Arg Asp Val Ala Arg Asn Phe Met Arg
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide

<400> SEQUENCE: 7

Arg Ser Arg Trp Arg Asp Trp Ser Arg Asn Phe Met Arg
 1               5                  10

<210> SEQ ID NO 8
<211> LENGTH: 27
<212> TYPE: PRT
<213> ORGANISM: Artificial Sequence
<220> FEATURE:
<223> OTHER INFORMATION: Synthetic peptide

<400> SEQUENCE: 8

Arg Ser Val Ser Asn Ala Ala Thr Arg Val Ser Arg Thr Gly Arg Ser
 1               5                  10                  15

Arg Trp Arg Asp Trp Ser Arg Asn Phe Met Arg
            20                  25

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Thr Arg Val Ala Arg Thr Gly Arg Ser Arg Trp Arg Asp Trp Ala Arg
 1               5                  10                  15

Asn Phe Met Arg
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

Thr Arg Val Asp Arg Thr Gly Arg Ser Arg Trp Arg Asp Trp Glx Arg
 1               5                  10                  15

Asn Phe Met Arg
            20

<210> SEQ ID NO 11
<211> LENGTH: 20
<212> TYPE: PRT
<213> ORGANISM: Artificial Sequence
```

```
<220> FEATURE:
<223> OTHER INFORMATION: Synthetic peptide

<400> SEQUENCE: 11

Thr Arg Val Ser Arg Thr Gly Arg Ser Arg Trp Arg Asp Val Ser Arg
1               5                   10                  15

Asn Phe Met Arg
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Thr Arg Val Ser Arg Thr Gly Arg Ser Arg Trp Arg Asp Trp Ser Arg
1               5                   10                  15

Asn Phe Met Arg
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Thr Arg Val Ser Arg Thr Gly Arg Ser Arg Trp Arg Asp Trp Ser Arg
1               5                   10                  15

Asn Phe Met Arg
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic peptide

<400> SEQUENCE: 14

Thr Arg Val Ser Arg Thr Gly Arg Ser Arg Trp Arg Asp Trp Ser Arg
1               5                   10                  15

Asn Phe Met Arg Ala Ala
            20

<210> SEQ ID NO 15
<211> LENGTH: 30
<212> TYPE: PRT
<213> ORGANISM: Artificial Sequence
<220> FEATURE:
<223> OTHER INFORMATION: Synthetic peptide

<400> SEQUENCE: 15

Thr Arg Val Ser Arg Thr Gly Arg Ser Arg Trp Arg Asp Trp Ser Arg
1               5                   10                  15

Asn Phe Met Arg Ala Ala Lys Lys Lys Lys Lys Lys Lys Lys
            20                  25                  30

<210> SEQ ID NO 16
<211> LENGTH: 21
<212> TYPE: PRT
<213> ORGANISM: Artificial Sequence
```

<220> FEATURE:
<223> OTHER INFORMATION: Synthetic peptide

<400> SEQUENCE: 16

Thr Arg Val Ser Arg Thr Gly Arg Ser Arg Trp Arg Asp Trp Ser Arg
1               5                   10                  15

Asn Phe Met Arg Asn
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic peptide

<400> SEQUENCE: 17

Thr Arg Val Ser Arg Thr Gly Arg Ser Arg Trp Arg Asp Trp Ser Arg
1               5                   10                  15

Asn Phe Met Arg Asn Trp
            20

<210> SEQ ID NO 18
<211> LENGTH: 22
<212> TYPE: PRT
<213> ORGANISM: Artificial Sequence
<220> FEATURE:
<223> OTHER INFORMATION: Synthetic peptide

<400> SEQUENCE: 18

Thr Arg Val Ser Arg Thr Gly Arg Ser Arg Trp Arg Asp Trp Ser Arg
1               5                   10                  15

Asn Phe Met Arg Asn Tyr
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic peptide

<400> SEQUENCE: 19

Thr Arg Val Ser Arg Thr Gly Arg Ser Arg Trp Arg Asp Trp Ser Arg
1               5                   10                  15

Asn Phe Met Arg Arg Arg
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic peptide

<400> SEQUENCE: 20

Thr Arg Val Ser Arg Thr Gly Arg Ser Arg Trp Arg Asp Trp Ser Arg
1               5                   10                  15

Asn Trp Met Arg Arg Arg
            20

<210> SEQ ID NO 21
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 21

Thr Arg Val Glx Arg Thr Gly Arg Ser Arg Trp Arg Asp Trp Asp Arg
1               5                   10                  15

Asn Phe Met Arg
            20

<210> SEQ ID NO 22
<211> LENGTH: 35
<212> TYPE: PRT
<213> ORGANISM: Artificial Sequence
<220> FEATURE:
<223> OTHER INFORMATION: Synthetic peptide

<400> SEQUENCE: 22

Gly Arg Asp Tyr Arg Thr Ser Leu Thr Ile Val Gln Lys Leu Lys Lys
1               5                   10                  15

Met Val Asp Lys Pro Thr Gln Arg Ser Val Ser Asn Ala Ala Thr Arg
            20                  25                  30

Val Ser Arg
        35

<210> SEQ ID NO 23
<211> LENGTH: 35
<212> TYPE: PRT
<213> ORGANISM: Artificial Sequence
<220> FEATURE:
<223> OTHER INFORMATION: Synthetic peptide

<400> SEQUENCE: 23

Thr Gly Arg Ser Arg Trp Arg Asp Val Ser Arg Asn Phe Met Arg Arg
1               5                   10                  15

Tyr Gln Ser Arg Val Ile Gln Gly Leu Val Ala Gly Glu Thr Ala Gln
            20                  25                  30

Gln Ile Ser
        35

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Gly Arg Asp Tyr Arg Thr Ser Leu Thr Ile Val Gln Lys Leu Lys Lys
1               5                   10                  15

Met Val Asp Lys
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

Lys Met Val Asp Lys Pro Thr Gln Arg Ser Val Ser Asn Ala Ala Thr
1               5                   10                  15

Arg Val Ser Arg
            20
```

-continued

```
<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Arg Asn Phe Met Arg Arg Tyr Gln Ser Arg Val Ile Gln Gly Leu Val
 1               5                  10                  15

Ala Gly Glu Thr
            20

<210> SEQ ID NO 27
<211> LENGTH: 14
<212> TYPE: PRT
<213> ORGANISM: Artificial Sequence
<220> FEATURE:
<223> OTHER INFORMATION: Synthetic peptide

<400> SEQUENCE: 27

Val Ala Gly Glu Thr Ala Gln Gln Ile Ser Glu Asp Leu Arg
 1               5                  10
```

GRANULYSIN PEPTIDES AND METHODS OF USE THEREOF

FEDERALLY SPONSORED RESEARCH AND DEVELOPMENT

This invention was made with Government support under Grant No. AR048551 awarded by the National Institutes of Health. The Government has certain rights in this invention.

BACKGROUND

Proteins present in cytoplasmic granules, including the pore-forming protein perforin, and a family of serine proteases called granzymes, have been implicated in granule mediated cytolysis. One of the proteins present in granules is the late T cell activation marker, granulysin. Granulysin is a 9 kDa arginine-rich protein, and is a member of a larger group of proteins, referred to as saposin-like proteins (sphingolipid activator protein like protein, SAPLIP). This family has been conserved for almost a billion years, from amoebas to humans. A subset of SAPLIP family members have antimicrobial activity. This subset includes NK-lysin, and amoebapores (which are used by amoebas to kill bacterial prey).

Granulysin is cytolytic against microbes and tumors. The crystal structure (see Anderson et al. (2003) J Mol. Biol. 325(2):355-65), suggests a mechanism for lysis of membranes. The five-helical bundle of granulysin resembles other "saposin folds". Positive charges distribute in a ring around the granulysin molecule, and one face has net positive charge. Sulfate ions bind near the segment of the molecule identified as most membrane-lytic and of highest hydrophobic moment. The ion locations may indicate granulysin's orientation of initial approach towards the membrane. The crystal packing reveals one way to pack a sheet of granulysin molecules at the cell surface for a concerted lysis effort. The energy of binding granulysin charges to the bacterial membrane could drive the subsequent lytic processes. The loosely packed core facilitates a hinge or scissors motion towards exposure of hydrophobic surface that is proposed to tunnel the granulysin into the fracturing target membrane.

By electron microscopy, granulysin has been shown to trigger fluid accumulation in the periplasm of M. tuberculosis, consistent with osmotic perturbation. These data suggest that the ability of granulysin to kill microbial pathogens is dependent on direct interaction with the microbial cell wall and/or membrane, leading to increased permeability and lysis.

Experiments have been performed (see Ernst et al. (2000) J. Immunol. 165:7102-7108) to correlate the structure and function of granulysin using biophysical approaches. Synthetic peptides of granulysin conforming to a putative helix-loop-helix motif (aa 1-35, 36-70, and 31-50) were shown to retain 50-80% of anti-bacterial activity, whereas those peptides without this predicted structure (aa 1-20, 16-35, 46-65, 61-80) had <20% activity. The structural model also predicts that the α helices are amphipathic, including 15 positively charged amino acids: 12 arginine (16%) and three lysine residues. Chemical modification of the arginine residues caused complete inhibition of the antimicrobial effects of granulysin; however, modification of the lysine residues did not inhibit the antimicrobial activity. Granulysin altered bacterial membranes by increasing their permeability, inducing lesions on the surface of bacteria and separation of the cell wall and membranes from the cytoplasm. These data suggest that the ability of granulysin to kill microbial pathogens is dependent on interactions with the microbial cell wall or membrane leading to increased permeability and osmotic lysis.

Since their introduction approximately 60 years ago, antibiotics have been our most powerful weapons against microbial invaders. However, the effectiveness of traditional antibiotics has been severely limited by the development of multidrug resistant bacterial strains. In particular, analysis of clinical isolates of *Propionibacterium acnes*, a major etiologic agent of acne vulgaris, has indicated increasing resistance to standard antibiotic therapies, making the treatment of acne more challenging. Thus, there is a need for the development of new antimicrobial agents for the treatment of acne and other diseases with an infectious component.

Relevant Literature

U.S. Pat. No. 4,994,369 discloses the nucleotide and predicted amino acid sequence of the "519" protein, which was subsequently named granulysin. The sequences of granulysin variants may be accessed from the Genbank and EMBL databases, with the accession number X05044 for the mRNA sequence of 519; EMBL accession X05044 for the encoded protein; and EMBL:locus HSNKG5, accession X54101 for the NKG5 splice variant.

The sequence and structure of the granulysin gene is discussed in Jongstra et al. (1987) J. Exp. Med. 165:601-614; Donlon et al. (1990) Cytogenet. Cell Genet. 53:230-231; and Manning et al. (1992) J. Immunol. 148:4036-4042.

The use of granulysin as an antimicrobial agent may be found in U.S. Pat. No. 6,485,928, issued Nov. 26, 2002. The activity of granulysin and derivative peptides is discussed, for example, by Stenger et al. (1998) Science 282(5386):121-5; Wang et al. (2000) J. Immunol. 165(3):1486-90; and Kumar et al. (2001) Expert Opin Investig Drugs 10(2):321-9.

SUMMARY OF THE INVENTION

Methods and compositions are provided for the use of granulysin peptides. Granulysin peptides, particularly modified granulysin peptides as described herein, are shown to have cytolytic activity against mammalian cells, including monocytes and keratinocytes. Of particular interest is the use of granulysin peptides for cytolysis of keratinocytes, e.g. in the treatment of warts, of benign and malignant skin cancers, treatment of psoriasis, etc.; and in the exfoliation of skin for cosmetic purposes, e.g. to reduce the appearance of fine lines and wrinkles, to reduce scarring, in the treatment of acne, and the like.

In one embodiment of the invention, the granulysin peptide contains an α-helix loop α-helix structure. Peptides of interest having such a structure include peptides of at least about 10 amino acids in length, falling within the sequence of residues 31-50 of the human granulysin protein, particularly including residues 38-50 of the human granulysin protein. The peptide is usually modified from the wild-type granulysin sequence by substitution of amino acid residues to increase hydrophobicity, e.g. substituting at position 44; at position 38, 40, 46, 47 and 50, etc. The peptide may be further substituted to replace cysteine residues present in the wild-type sequence with a small non-polar or neutral amino acid, e.g. e.g. alanine, threonine, serine, glycine, etc. It is shown herein that acylated derivatives are cytolytically active against skin cells, i.e. keratinocytes. Acyl groups of interest for modification include lauryl, myristyl, palmitoyl, decyl and stearyl groups.

Formulations of granulysin peptides include cosmetic formulations, where the granulysin peptide may be combined with exfoliating agents, e.g. α-glycolic acids, salicylic acid, azaleic acid, retinoids, etc. Such cosmetic formulations may be provided in a gel, cream, lotion, and the like, and may further comprise emollients, sun-blocking agents, and the like.

In another embodiment, formulations of granulysin include pharmaceutical formulations, particularly topical pharmaceutical formulations, for the cytolysis of keratinocytes. Such formulations comprise pharmaceutically acceptable excipients, and may be formulated for topical use, intra-lesional injection, and the like. Such formulations may further comprise agents active in the treatment of skin growth and cancers, e.g. aminolevulinic acid, salicylic acid, cantharidin, dichloroacetic acid, 5-fluorouracil, corticosteroids, psoralens, etc., which are, in some instances, optionally combined with photodynamic treatment.

DESCRIPTION OF THE SPECIFIC EMBODIMENTS

Figure 1:
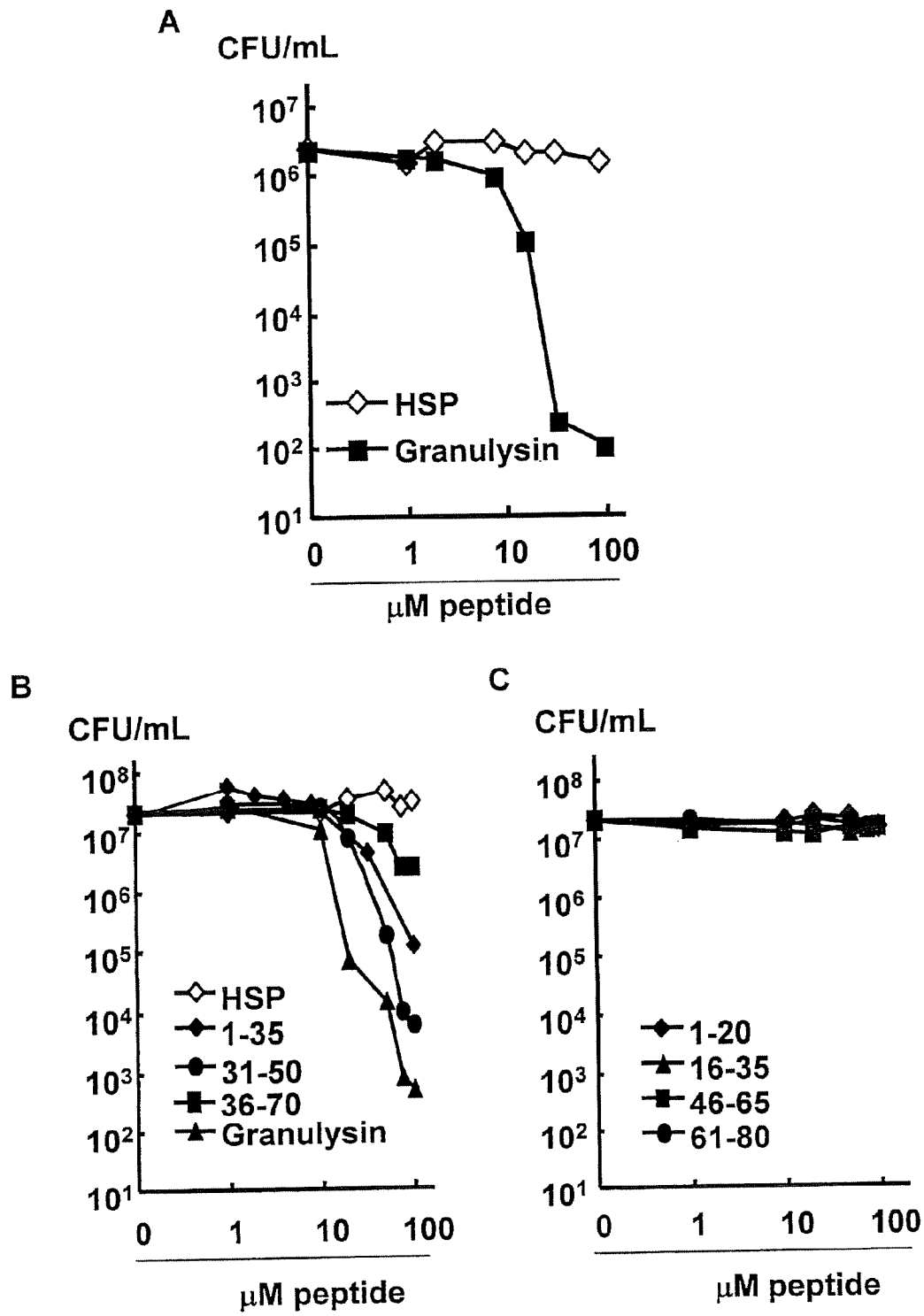
FIG. 1. Granulysin and granulysin peptides have antimicrobial activity against *P. acnes*. (A) Various concentrations (0-100 µM) of recombinant granulysin were incubated with *P. acnes* for four hours and tested for antimicrobial activity using the CFU assay. (B) Synthetic peptides of granulysin predicted to conform to a helix-loop-helix motif (residues 1-35, 36-70, and 31-50) and the 9-kDa granulysin were incubated with *P. acnes* at various concentrations (0-100 µM) for four h and the antimicrobial activity was determined by CFU assay. (C) Additional synthetic granulysin peptides (residues 1-20, 16-35, 46-65, and 61-80) were compared with the 9-kDa granulysin for antimicrobial activity by CFU assay.

Methods are provided for the use of granulysin fragments and granulysin analogs, herein referred to as granulysin peptides, as therapeutic and/or prophylactic agents. Methods of cutaneous application are of particular interest.

In some methods, granulysin peptides are used for topical cytolysis of keratinocytes, e.g. in the treatment of warts, of benign and malignant skin cancers, treatment of psoriasis, etc.; and in the exfoliation of skin for cosmetic purposes, e.g. to reduce the appearance of fine lines and wrinkles, to reduce scarring, in the treatment of acne, and the like. Granulysin peptides are administered alone or in combination with other active agents to a patient in a dose and for a period of time sufficient to reduce the undesirable keratinocytes.

Granulysin fragments useful in the methods of the invention include peptides derived from a granulysin sequence, of at least about 10 amino acids in length, which comprise an α-helix turn α-helix structure, and derivatives thereof. Derivatives of interest comprise an amino acid substitution in at least one position, which increases the hydrophobicity of the peptide, and may further comprise a substitution of cysteine residues. Peptides may be acetylated and/or amidated. These peptides are also cytolytic against keratinocytes and monocytes, and are also effective at killing a variety of microbial organisms, including microbes responsible for cutaneous infections.

Granulysin peptides may be used for topical application onto the skin of a human subject. The peptides have cytolytic activity against keratinocytes, and thus are therapeutically useful exfoliative agents for a variety of cosmetic and therapeutic purposes. Indications for use include the treatment of acne, in which hyperproliferation that leads to comedonal lesions play a role in the pathogenesis of acne. The cytolytic activity of these peptides against keratinocytes makes them useful for treatment of common skin cancers, and warts. The combined anti-inflammatory activity and cytolytic against keratinocytes makes them useful in the treatment of psoriasis.

Granulysin Compositions

For use in the subject methods, granulysin peptides comprising an α-helix turn α-helix structure, of at least about 10 amino acids, usually at least about 12 amino acids, at least about 15 amino acids, and which include, without limitation, peptides consisting of, or comprising residues 1-35, 36-70; 42-51; 31-50; 38-50 of human granulysin, and modifications thereof. A combination of one or more forms may be used. The granulysin sequence may be from any mammalian or avian species, e.g. primate sp., particularly humans; rodents, including mice, rats and hamsters; rabbits; equines, bovines, canines, felines; etc. Of particular interest are the human proteins. Preferably the peptide is modified to comprise an acyl group.

The naturally occurring form the 31-50 peptide of human qranulysin has the sequence, (SEQ ID NO:1):

```
T   R   V   C   R   T   G   R   S   R   W   R   D   V   C   R   N
31  32  33  34  35  36  37  38  39  40  41  42  43  44  45  46  47

F   M   R
48  49  50
```

In one embodiment, the peptide composition is a derivative of 31-50, 38-50, or 42-51, which has been modified to increase hydrophobicity. Hydrophobic amino acid substitutions of interest include peptides comprising a substituted amino acid at position 44, e.g. substituting the val (V) for a more hydrophobic amino acid, e.g. M, F, W or C. 44W is exemplary, but those of skill in the art can readily substitute this position with other hydrophobic residues. Other residues that may be substituted with a hydrophobic amino acid as recited above are the arg (R) residues at positions 32, 35, 38, 40, 46 and 50; and the asp (N) at position 47. A preferred peptide comprises at least one amino acid substitution that increases the hydrophobicity of the peptide, and may comprise one, two three, four or more hydrophobic substitutions.

Peptides of interest may further comprise amino acid substitution(s) at naturally occurring cysteine residues, for example at one or more of positions 7, 34, 45 and 70 of the human granulysin sequence. Cysteine substitutions of particular interest include small polar or neutral amino acids, e.g. alanine, threonine, serine, glycine, etc.

In one embodiment of the invention, the peptide comprises a sequence chosen from: SEQ ID NO:2 AATRVSRTGRSRWRDWSRNFMR; SEQ ID NO:3 ERVSRTGRSRWRDWSRNFMRRR; SEQ ID NO:4 RRVSRTGRSRWRDWSRNFMRRR; SEQ ID NO:5 RSRWRDVARNFMR; SEQ ID NO:6 RSRWRDVARNFMR; SEQ ID NO:7 RSRWRDWSRNFMR; SEQ ID NO:8 RSVSNAATRVSRTGRSRWRDWSRNFMR; SEQ ID NO:9 TRVARTGRSRWRDWARNFMR; SEQ ID NO:10 TRVDRTGRSRWRDWZRNFMR; SEQ ID NO:11 TRVSRTGRSRWRDVSRNFMR; SEQ ID NO:12 TRVSRTGRSRWRDWSRNFMR; SEQ ID NO:14 TRVSRTGRSRWRDWSRNFMRAA; SEQ ID NO:15 TRVSRTGRSRWRDWSRNFMRAAKKKKKKKK; SEQ ID NO:16 TRVSRTGRSRWRDWSRNFMRN; SEQ ID NO:17 TRVSRTGRSRWRDWSRNFMRNW; SEQ ID NO:18 TRVSRTGRSRWRDWSRNFMRNY; SEQ ID NO:19 TRVSRTGRSRWRDWSRNFMRRR; SEQ ID NO:20 TRVSRTGRSRWRDWSRNWMRRR; SEQ ID NO:21 TRVZRTGRSRWRDWDRNFMR; where the peptides may be modified, e.g. acylated, acetylated, amidated, and may be L amino acids or D-amino acids. Modifications of interest include addition of an acyl group, e.g. lauryl, myristyl, palmitoyl, decyl and stearyl groups on the N-terminal end of the peptides.

In one embodiment of the invention, the peptide is SEQ ID NO:12 TRVSRTGRSRWRDWSRNFMR (31-50v44w), which may be acylated, e.g. as (lauryl-31-50v44w). In another embodiment, the peptide is a D-amino acid form (D-31-50v44w), or an acylated D-amino acid form, e.g. (Lauryl-D-31-50v44w). In another embodiment, the peptide is SEQ ID NO:5 RSRWRDVARNFMR (38-50s45a), which may be acylated, e.g. as (lauryl-38-50s45a). In another embodiment, the peptide is in the D-amino acid form (D-38-50s45a), which may be acylated, e.g. as (D-lauryl-38-50s45a).

The nucleic acid sequences encoding the above human granulysin polypeptides may be accessed from public databases or the sequence listing as previously cited. Identification of non-human granulysins is accomplished by conventional screening methods of DNA libraries or biological samples for DNA sequences having a high degree of similarity to known granulysin sequences.

As described above, the sequence of granulysin peptides may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet. 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins, such as the Fc of an IgG isotype, which may be complement binding, with a toxin, such as ricin, abrin, diphtheria toxin, or the like, or with specific binding agents that allow targeting to specific moieties on a target cell.

The granulysin for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acetylation, amidation, carboxylation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are peptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the antimicrobial peptide consists essentially of a polypeptide sequence of at least 10 amino acids in length and having a sequence within residues 31-50; 38-50, or 42-51 of human granulysin, further comprising at least one hydrophobic amino acid substitution as described above, and usually comprising substitution of cysteine residues as described above. By "consisting essentially of" in the context of a polypeptide described herein, it is meant that the polypeptide is composed of the granulysin sequence, which sequence may be flanked by one or more amino acid or other residues that do not materially affect the basic characteristic(s) of the polypeptide.

The invention includes nucleic acids encoding the peptides of the invention. Granulysin coding sequences can be generated by methods known in the art, e.g. by in vitro synthesis, recombinant methods, etc. to provide a coding sequence to corresponds to a granulysin polypeptide that can serve as an intermediate in the production of the granulysin peptide. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

Granulysin encoding nucleic acids can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce a granulysin coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The nucleic acid may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold microprojectiles are coated with the stresscopin or DNA, then bombarded into skin cells.

Conditions for Treatment

Psoriasis is a chronic skin disease, characterized by scaling and inflammation. Psoriasis affects 1.5 to 2 percent of the United States population, or almost 5 million people. It occurs in all age groups and about equally in men and women. People with psoriasis suffer discomfort, restricted motion of joints, and emotional distress. When psoriasis develops, patches of skin thicken, redden, and become covered with silvery scales, referred to as plaques. Psoriasis most often occurs on the elbows, knees, scalp, lower back, face, palms, and soles of the feet. The disease also may affect the fingernails, toenails, and the soft tissues inside the mouth and genitalia. About 10 percent of people with psoriasis have joint inflammation that produces symptoms of arthritis.

When skin is wounded, a wound healing program is triggered, also known as regenerative maturation. Lesional psoriasis is characterized by cell growth in this alternate growth program. In many ways, psoriatic skin is similar to skin healing from a wound or reacting to a stimulus such as infection, where the keratinocytes switch from the normal growth program to regenerative maturation. Cells are created and pushed to the surface in as little as 2-4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

The chronic skin inflammation of psoriasis is associated with hyperplastic epidermal keratinocytes and infiltrating mononuclear cells, including CD4+ memory T cells, neutrophils and macrophages. Because of this highly mixed inflammatory picture and the resulting complex interrelationships between these different cells, it has been difficult to treat this disease.

The severity of psoriasis is measured by the Psoriasis Area Severity Index (PASI) (see e.g., Fleischer et al. (1999), J. Dermatol. 26:210-215 and Tanew et al. (1999), Arch Dermatol. 135:519-524) or various psoriasis global assessment scores such as Physician's Global Assessment (PGA) which are well-known to those skilled in the art of clinical trials for psoriasis. Topical treatment with granulysin peptides can reduce the PASI (or global assessment score) by at least 25% or 40% but preferably 50% or even 60 or 70% or more in at least 50% but preferably 60-70% or 75% or more of the patients treated. Alternatively, such treatment will cause a greater reduction in a smaller group or patients, i.e., at least 75% but preferably 80-90% or more or even essentially complete clearance, in at least 20% to 25% but preferably 30% to 40% or even 50% or more of the patients. This reduction will typically last at least 2 but preferably 3 or more months, or even 4 to 6 or more months, but most preferably a year or longer, either while treatment is continued or after it is stopped. Typically, in a clinical trial (e.g., a phase II or phase III trial), the improvement in PASI or score in the patients treated with the peptide, relative to the control group of patients receiving no treatment or placebo or another agent, will be statistically significant, for example at the p=0.05 or 0.01 or even 0.001 level.

Alternatively, the peptides can be administered after remission has already been induced by another drug, for example corticosteroids, cyclosporine, methotrexate, phototherapy (with or without PUVA) or others. In this case, treatment with the peptides will increase the median time to relapse (e.g., 50% worsening in PASI) by at least 40% but preferably 50% and most preferably 60-70% or more or even 100% (doubling) or more. Typically, in a clinical trial (e.g., a phase II or phase III trial), this increase of time to relapse in the patients treated with the granulysin treatment, relative to the control group of patients receiving no treatment or placebo or another agent, will be statistically significant, for example at the p=0.05 or 0.01 or even 0.001 level.

Skin Cancers

Basal cell carcinoma is the most common type of skin cancer, with >400,000 new cases yearly in the USA. It is more common in fair-skinned, sun-exposed persons. The clinical presentation and biologic behavior of basal cell carcinomas are highly variable. They may appear as small, shiny, firm, almost translucent nodules (see Plate 126-1); ulcerated, crusted papules or nodules; flat, scarlike indurated plaques; or red, marginated, thin papules or plaques difficult to differentiate from psoriasis or localized dermatitis. Most commonly the carcinoma begins as a shiny papule, enlarges slowly, and, after a few months or years, shows a shiny, pearly border with prominent engorged vessels (telangiectases) on the surface and a central dell or ulcer. Recurrent crusting or bleeding is not unusual, and the lesion continues to enlarge slowly. Commonly, the carcinomas may alternately crust and heal, which may decrease the patient's and physician's concern about the importance of the lesion. Basal cell carcinomas rarely metastasize but may invade healthy tissues. Rarely, death may ensue because the carcinoma invades or impinges on underlying vital structures or orifices (eyes, ears, mouth, bone, dura mater). Treatment should be performed by a specialist after mandatory biopsy and histologic examination.

Squamous cell carcinoma, the second most common type of skin cancer, may develop in normal tissue, in a preexisting actinic keratosis or patch of leukoplakia, or in burn scars. The incidence in the USA is 80,000 to 100,000 cases annually. The clinical appearance is highly variable. The tumor may begin as a red papule or plaque with a scaly or crusted surface and may become nodular, sometimes with a warty surface. In some, the bulk of the lesion may lie below the level of the surrounding skin. Eventually it ulcerates and invades the underlying tissue. The percentage of squamous cell carcinomas on sun-exposed skin that metastasize is quite low. However, about ⅓ of lingual or mucosal cancers have metastasized before diagnosis. A biopsy is essential. In general, the prognosis for small lesions removed early and adequately is excellent. Treatment is the same as for basal cell carcinoma.

Malignant melanoma is a malignant melanocytic tumor arising in a pigmented area: skin, mucous membranes, eyes, and CNS. About 25,000 new cases of malignant melanoma occur yearly in the USA, causing about 6000 deaths. The incidence is rising rapidly. Sun exposure is a risk, as is family history and the occurrence of lentigo maligna, large congenital melanocytic nevus, and the dysplastic nevus syndrome. Malignant melanomas vary in size, shape, and color (usually pigmented) and in their propensity to invade and metastasize. This neoplasm may spread rapidly, causing death within months of its recognition, yet the 5-yr cure rate of early, very superficial lesions is nearly 100%. Thus, cure depends on early diagnosis and early treatment.

Lentigo maligna melanoma arises from lentigo maligna; it appears on the face or other sun-exposed areas usually in elderly patients as an asymptomatic, 2- to 6-cm, flat, tan or brown, irregularly shaped macule or patch with darker brown or black spots scattered irregularly on its surface. In lentigo maligna, both normal and malignant melanocytes are confined to the epidermis; when malignant melanocytes invade the dermis, the lesion is called lentigo maligna melanoma and the cancer may metastasize.

Superficial spreading melanoma accounts for ⅔ of malignant melanomas. Usually asymptomatic, it is usually diagnosed when smaller than lentigo maligna melanoma and occurs most commonly on women's legs and men's torsos. The lesion is usually a plaque with irregular raised, indurated tan or brown areas, which often show red, white, black, and blue spots or small, sometimes protuberant, blue-black nodules. Small notchlike indentations of the margins may be noted, along with enlargement or color change. Histologically, atypical melanocytes characteristically invade dermis and epidermis.

Nodular melanoma constitutes 10 to 15% of malignant melanomas. It may occur anywhere on the body as a dark, protuberant papule or a plaque that varies from pearl to gray to black. Occasionally, a lesion contains little if any pigment or may look like a vascular neoplasm. Unless it ulcerates, nodular melanoma is asymptomatic, but the patient usually seeks advice because the lesion enlarges rapidly.

Acral-lentiginous melanoma arises on palmar, plantar, and subungual skin and has a characteristic histologic picture similar to lentigo maligna melanoma.

For treatment of such skin cancers, topical or intra-lesional treatment with granulysin peptides may be combined with surgery, irradiation (e.g. in combination with aminolevulinic acid, psoralens, etc.), and/or chemotherapy, e.g. treatment with 5-fluorouracil, cisplatin, etc. Treatment will be performed at a dose and for a length of time sufficient to reduce the number of transformed cells present in the lesion. This reduction will typically last at least 2 but preferably 3 or more months, or even 4 to 6 or more months, but most preferably a year or longer, either while treatment is continued or after it is stopped. Therapy with granulysin in a combined therapy will generally provide for enhanced efficacy relative to monotherapy.

Benign Skin Growths

Benign skin growths include moles, warts, etc. Moles are circumscribed pigmented macules, papules, or nodules composed of clusters of melanocytes or nevus cells. They may be small or large; flesh-colored, yellow-brown, or black; flat or raised; smooth, hairy, or warty; broad-based or pedunculated. Moles can be removed for cosmetic purposes. Dysplastic nevi are pigmented lesions, often rather large, with borders that are usually irregular and ill-defined, with variegated colors usually of brown and tan tones, and with macular or papular components. Seborrheic Warts are pigmented superficial epithelial lesions that are usually warty but may occur as smooth papules. Seborrheic keratoses vary in size and grow slowly. They may be round or oval or flesh-colored, brown, or black; usually appear "stuck on"; and may have a verrucous, velvety, waxy, scaling, or crusted surface. They are not premalignant and need no treatment unless they are irritated, itchy, or cosmetically bothersome. Keratoacanthoma is a round, firm, usually flesh-colored nodule with sharply sloping borders and a characteristic central crater containing keratinous material. Onset is rapid; usually within 1 or 2 mo the lesion reaches its full size, which may be >5 cm. Common sites are sun-exposed areas, the face, the forearm, and the dorsum of the hand.

For treatment of such skin benign skin lesions, topical or intra-lesional treatment with granulysin peptides may be combined with surgery, irradiation (e.g. in combination with aminolevulinic acid, psoralens, etc.), and/or treatment with agents such as α-glycolic acids, salicylic acid, azaleic acid, retinoids, α-levulinic acid, salicylic acid, cantharidin, dichloroacetic acid, 5-fluorouracil, etc. Treatment will be performed at a dose and for a length of time sufficient to reduce the number of cells present in the lesion. This reduction will typically last at least 2 but preferably 3 or more months, or even 4 to 6 or more months, but most preferably a year or longer, either while treatment is continued or after it is stopped. Therapy with granulysin in a combined therapy will generally provide for enhanced efficacy relative to monotherapy.

Cosmetic Conditions

The compositions and methods of the invention also find for skin exfoliation. The cells of the outermost layer of the stratum corneum are constantly shed naturally, by the normal process of desquamation, as minute particles. When fully keratinised tissue loses its cellular structure and reaches the surface of the stratum corneum, it breaks up into microscopic squames and sheds off the surface of the skin. Microscopic squames at the skin surface are commonly referred to as dead skin cells and make up a dead skin layer on the skin surface. The process of desquamation has been estimated to cause a loss of tissue in an amount of up to 14 grams per day. This loss is constantly replenished with cells from lower layers of the epidermis. Thus, the layers of the epidermis are composed of cells moving up towards the surface in successive stages of differentiation until death when they are finally sloughed offend lost to the environment. Desquamation is one of the processes by which skin maintains its health and vitality as nutrients and moisture are continuously replaced on the surface of the skin when dead skin cells are removed. Normally, the desquamation process takes about 14 days. When desquamation does not take place regularly, the surface of the skin tends to become rough and flaky, and wrinkles as well as other undesirable effects of skin aging may appear on the surface of the skin. To improve these skin conditions, in addition to or as an alternative to the natural desquamation process, exfoliation may be used to rejuvenate and enhance the health of the skin at any age.

To exfoliate the epidermis, compositions containing granulysin peptides are applied to the skin in a topical manner, and for a period of time sufficient for the peptides to act on the skin cells. The composition is optionally removed with washing, mild physical abrasion, and the like. Optionally, other exfoliating agents are included, for example, alpha hydroxy acid ("AHA"), beta hydroxy acid ("BHA"), retinoic acid ("retin A"), salicylic acid, azaleic acid, etc.

Alpha-hydroxy acids, e.g. lactic acid, may be used to help smooth the signs of aging, improve skin's texture and softness, reduce the appearance of fine lines and wrinkles, fade surface discoloration, reduce oiliness, unclog pores, and clear blemishes. Alpha-hydroxy acids or exfoliating ingredients may be used to exfoliate old dry cells so that the composition may penetrate underlying cells with greater efficiency.

In another embodiment, the exfoliating activity of granulysin is used in the treatment of acne, where a peptide composition may be applied topically or intra-lesionally to the affected areas. Formulations for acne treatment may be combined with other agents, e.g. alpha hydroxy acid ("AHA"), beta hydroxy acid ("BHA"), retinoic acid ("retin A"), salicylic acid, azaleic acid, etc.

Other embodiments include ingredients for supplying moisture and hydration to the skin. Sodium hyaluronate and hyaluronic acid can be used to hydrate the skin and tissues of the lips. Because hyaluronic acid can hold up to approximately 1000 times its own weight in moisture, it can be used to supply moisture to the lip tissues. Amino acids, fucogel, and glycoaminoglycan can be used to draw and lock water into tissues for increased hydration. Pectins may also be used to retain moisture. Omega 3, 6 and 9 fatty acids may be used. Chamomile extract can help sooth and hydrate tissues. Any suitable oils, moisturizers and hydration stimulating ingredients may be used. Tocopheryl acetate (vitamine E) can be used to keep skin oils fresh. Any suitable forms of tocopherols (gamma, delta, beta, and d-alpha tocopherol, including d-alpha tocopherol acid succinate for example) and, or any suitable forms of tocotrienols, (d-alpha, d-beta, d-gamma and d-delta tocotrienol for example), or any other suitable forms of vitamin E or their derivatives may be used as well. Algae peptides may be used to improve moisturization and hydration to the skin. UVA/UVB sun screens may also be used to prevent tissue damage, dehydration, photo aging, and sunburn. UV protectants can include organic and non-organic ingredients such as sodium cocoyl aminoacids, octinoxate, oxybenzone, octisalate, avobenzone, homosalate, sarcosine, potassium aspartate, magnesium aspertate, titanium dioxide, Parisol 1789®, coffee extracts, coral extracts as well as any other suitable sunscreens or UV inhibitors.

Other moisturizing or hydrating ingredients can include emu oil, aquaphor, dipalmitoyl, plankton, *helianthus annuus* (sunflower) seed oil, *carthamus tinctorius* (safflower) seed oil, *persea gratissima* (avocado) oil, *symphytum officinale* extract, *cucumis stivus* (cucumber) fruit extracts, *hedera helix* (ivy) extract, *coffea arabica* (coffee) extract, *viola tricolor* extract, cydomethican, *commiphora myrrha* oil, mirth extract, *cymbopogon schoenanthus* oil, *salvia officinalis* (sage) oil, petrolatum, lanolin, hydrolyzed lupin extract, royal jelly, hydrolyzed rice extract, vegetable oil, mineral oil, citrus oils, japan wax, oatmeal, caprylic/capric triglycerides, methylparaben, propylparaben, aloe barbadensis leaf extracts, aloe vera juice, glycine (soybean), paraffin wax, microcrystalline wax, vorexin complex, peanut oil, monoi oils, flax seed oil, biotin, almond oil, almond extract, walnut oil, walnut extract, sunflower seed oil, macadamian nut oil, moringa oleifera, lanolin, castor oil, babassu oil orbignya oleifera), apricot kernal oil, shea, shea butter, cocoa butter (*theobroma cacao*), beeswax (cera alba), lamolin wax, paraffin wax, other suitable waxes, hydrolized soy protein, hydrolyzed whey protein, egg protein, soy protein, distilled water, spring water, mineral water, salt water, purified water, kelp extracts, kelp protein, seaweed extracts, lecithin, camphor, xanthum gum, grape seed oil, jojoba oil, glycol, white lilly gel, coconut oils, gelatins, moisturizing colloids, caster oil, glycerin, mineral oil, mink oil, petrolatum, *mortierella* Oil, arginine hydrochloride, hydrolyzed keratin, sunflower (*Helianthus Annuus*), ylang ylang (*Cananga Odorata*) oil, rosemary (*Rosmarinus Officinalis*) Oil, Niaouli (*Melaluca Viridiflora*) Oil, Bergamot (*Citrus aurantium bergamia*) oil, cypress (*Cupressus Sempervirents*) oil, lemon (*citrus medica limonum*) oil, bitter orange (*citrus aurantium amara*) oil, lavender (*lavandula hybrida*) oil, *rosa centifolia* oil, corn oil, (sage) leaf oil, melaleuca leucadendryon cajaputi oil, plant extracts, seed extracts, or any suitable organic and inorganic compound capable of providing a moisturizing effect to the skin or surrounding tissues.

Methods of Use

Formulations of granulysins as described above are administered to a host suffering from skin conditions as described above, including bacterial infections as found in acne. Cutaneous, e.g. topical, intra-lesional, etc. administration is of particular interest. It is contemplated that the composition will be obtained and used under the guidance of a physician for in vivo use. Granulysin peptides are particularly useful for killing *Propionibacterium acnes*.

The susceptibility of a particular cell to killing or inhibition by granulysins may be determined by in vitro testing, as detailed in the experimental section. Typically a culture of the cells is combined with granulysins at varying concentrations for a period of time sufficient to allow the protein to act, usually ranging from about one hour to one day. The viable cells are then counted, and the level of killing determined. Two stage radial diffusion assay is a convenient alternative to determining the MIC or minimum inhibitory concentration of an antimicrobial agent.

Various methods for administration may be employed. The polypeptide formulation may be given topically, orally, or may be injected, e.g. intra-lesionally, subcutaneously, peritoneally, by aerosol, opthalmically, intra-bladder, topically, etc. For example, methods of administration by inhalation are well-known in the art. The dosage of the therapeutic formulation will vary widely, depending on the specific granulysin peptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration.

Formulations

The compounds of this invention can be incorporated into a variety of formulations for therapeutic or cosmetic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols.

The compounds of the present invention can be administered alone, in combination with each other, or they can be used in combination with other known compounds (e.g., perforin, anti-inflammatory agents, antibiotics, retinoids, etc.) In pharmaceutical dosage forms, the compounds may be administered in the form of their pharmaceutically acceptable salts. The following methods and excipients are merely exemplary and are in no way limiting.

Topical compositions are provided for exfoliating treatment of wrinkles and fine lines; acne, treatment of skin cancers, and inflammation of the skin. The skin care compositions comprise an effective dose of a granulysin peptide, usually an acylated granulysin peptide, and a cosmetically acceptable vehicle. The dose of granulysin present in a topical composition may be at least about 0.1 µM, at least about 1 µM, at least about 10 µM, at least about 100 µM, at least about 1 mM, at least about 10 mM. Generally, compositions for treatment of skin cancers and benign lesions will be utilized at a higher concentration, e.g. at least about 10 µM, at least about 100 µM, at least about 1 mM, at least about 10 mM, while cosmetic formulations may use lower concentrations, e.g. at least about 0.1 µM, at least about 1 µM.

A typical dose for a topical formulation is from about 1 µl to about 100 µl to about 1 ml, to about 10 ml, applied in a lotion, cream, gel, etc. to the affected skin. In use, a small quantity of the composition is applied to exposed areas of the skin, from a suitable container or applicator and, if necessary, it is then spread over and/or rubbed into the skin using the hand or fingers or a suitable device. The product may be specifically formulated for use as a hand, or as a facial treatment.

A typical dose for a therapeutic purpose may be from about 0.1 µl, about 1 µl, about 10 µl, about 100 µl or more, and may be delivered topically or by injection to the targeted lesion, e.g. wart, carcinoma, acne, etc.

The compositions of the invention find use in improving the appearance of fine lines and wrinkles, pigmentation, scars, e.g. in sun-damaged skin, etc. The compositions may also be used in the treatment of irritated skin, e.g. minor rashes and burns. Further examples of minor skin irritations include acne, cold sores, insect bites and other inflammatory and non-inflammatory lesions of the skin.

Cosmetic Formulations

The cosmetic compositions of the invention may optionally comprise other skin benefit materials. These include estradiol; progesterone; pregnanalone; coenzyme Q10; kinetin; idebenone; vitamin C; vitamin E; methylsolanomethane (MSM); copper peptide (copper extract); plankton extract (phytosome); glycolic acid; kojic acid; ascorbyl palmitate; all-trans-retinol; azaleic acid; salicylic acid; broparoestrol; estrone; adrostenedione; androstanediols; etc. The steroids will generally present at a concentration of less than about 2% of the total by weight of the composition, while the other skin benefit materials may be present at higher levels, for example as much as 10 to 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used, and/or zinc and titanium. The exact amount of sunscreen employed in the compositions can vary depending upon the degree of protection desired from the sun's UV radiation.

The compositions of the invention comprise a cosmetically acceptable vehicle to act as a dilutant, dispersant or carrier, so as to facilitate granulysin distribution when the composition is applied to the skin. Vehicles other than or in addition to water can include liquid or solid emollients, solvents, humectants, thickeners and powders.

The cosmetically acceptable vehicle will usually form from 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifer and coemulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase, into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

Pharmaceutical Formulations

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms such as lotions, syrups, elixirs, and suspensions may be provided wherein each dosage unit contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing granulysins is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwifterionic lipids, such as phosphatidylcholine. The remaining lipid will be normally be neutral or acidic lipids, such as cholesterol, phosphatidyl serine, phosphatidyl glycerol, and the like.

Formulations with Other Active Agents

For use in the subject methods, granulysins may be formulated with other pharmaceutically active agents, particularly other chemotherapeutic agents; other exfoliating agents; other anti-inflammatory agents, or other antimicrobial agents.

Exfoliating agents of interest include alpha hydroxy acid ("AHA"), beta hydroxy acid ("BHA"), retinoic acid ("retin A"), salicylic acid, azaleic acid, dichloroacetic acid, etc.

Chemotherapeutic agents of interest include cisplatin, methotrexate, 5-fluorouracil, aminolevulinic acid, cantharidin, etc.

Anti-inflammatory agents include corticosteroids, e.g. Clobetasol propionate, betamethasone dipropionate, betamethasone valerate, betamethasone dipropionate, diflucortolone valerate, fluticasone valerate, hydrocortisone 17-butyrate, mometasone furoate, methylprednisolone aceponate, aclometasone dipropionate, clobetasone butyrate, fluocinolone acetonide, triamcinolone acetonide, hydrocortisone, etc. Nonsteroidal anti-inflammatory drugs (NSAIDs) include ibuprofen, piroxicam, salicylate, aspirin, naproxen, indomethacin, diclofenac, or any mixture thereof. Also of interest are NSAIDs, such as fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac tromethamine, nabumetone, sulindac, tolmetin sodium, fenamates, meclofenamate sodium, mefenamic acid, piroxicam, salicylic acid, diflunisal, aspirin, oxyphenbutazone, and phenylbutazone.

Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Cytokines may also be included in a granulysin formulation, e.g. interferon γ, tumor necrosis factor α, interleukin 12, etc.

Antiviral agents, e.g. acyclovir, gancyclovir, etc. may also be included in granulysin formulations.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a granulysin formulation, e.g. interferon γ, tumor necrosis factor α, interleukin 12, etc.

Granulysin peptides may be formulated with anti-inflammatory drugs and herbal medicines. Herbal medicines of interest include, but not restricted to, active fractions from certain herbal preparations such as nettles (*Urtica dioica*) or turmeric (*Curcuma longa*); marine or terrestial animal products, e.g. bioactive lipids from *Perna canaliculus, Dromaius nova hollandiae*, etc. In addition, other known synergists, e.g. stable prostaglandin analogues such as misoprostol, etc., may potentiate the therapeutic effects.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Conventional antibiotics are currently used for skin infections. However, the increase in antibiotic-resistant strains of Gram-positive bacteria has hastened research for development of novel therapeutic agents. Evidence is provided herein demonstrating that the body's own natural antimicrobial peptides are useful therapeutic agents in the treatment of skin infections and for cytolysis of keratinocytes.

Example 1

Methods

Production and purification of recombinant granulysin. Granulysin was produced in *Escherichia coli* BL21 (DE3) transformed with the kanamycin-selective vector, pET28, containing a hexahistidine fusion tag (Novagen, Madison, Wis.) as previously described (Pena et al., 1997; Ernst et al., 2000). The transformed *E. coli* were grown in 2×YT broth and induced with 1 mM isopropyl-β-D-thiogalactoside (Fisher Scientific, Pittsburgh, Pa.). The bacteria were harvested and denatured in 6 M guanidine HCl/0.05 mM Tris HCl pH 7.4. Granulysin was purified via nickel affinity chromatography according to the manufacturer's recommendation (Qiagen, Valencia, Calif.) and eluted with 0.2 M imidazole, then reduced with 10 mM DTT. The denatured granulysin was renatured in 0.75 M arginine, 0.05 M Tris HCl pH 8.0, 0.05 M KCl, 0.1 mM EDTA, and 10 mM oxidized DTT at a 1:5 dilution with constant stirring for 48 hours at 4° C. The re-natured protein was then dialyzed against a buffer containing 2 mM sodium phosphate and 13 mM sodium chloride pH 7.2, then lyophilized. The granulysin pellet was rehydrated and treated with thrombin for 16 h to cleave the hexahistidine tag. Following thrombin cleavage, the protein was loaded onto a Rainin $C_{18}$ reverse phase chromatography column (Braintree, Mass.) and eluted by a linear gradient of 10-60% aqueous acetonitrile in 0.1% trifluoroacetic acid. The fractions containing granulysin, as determined by Coomassie staining of a 15% SDS-PAGE gel, were lyophilized then hydrated in 10 mM sodium phosphate pH 7.2 unless otherwise noted. The final protein concentration was determined using the bicinchoninic acid protein assay (Pierce, Rockford, Ill.) with bovine serum albumin as a standard. Protein purity was assessed by Coomassie staining of 15% SDS-PAGE gels and was >95%. Additionally, purified granulysin was analyzed by matrix-assisted laser desorption ionization mass spectrometry and shown to contain one species at 9081 Da that corresponded to the calculated mol wt, which is 9070.4 assuming that four of the five cysteines are involved in disulfide bridges.

Peptide synthesis. Peptides encompassing the entire amino acid sequence of granulysin were synthesized using F-moc chemistry by either an Applied Biosystems (Foster City, Calif.) or UCLA Peptide Core (Los Angeles, Calif.) automatic peptide synthesizer and were purified to >95% homogeneity by reverse phase HPLC, and peptide composition was confirmed by mass spectrometry and amino acid analysis. Stock peptide solutions were prepared at 20 mg/ml in DMSO or at 2 mM in water. To construct a peptide containing amino acid residues 62-74, additional sequence from the 15-kDa form of granulysin was used to generate the 61-80 peptide so the length of this peptide would be similar to the others in our study.

Serine residues were also substituted for the protein's native cysteine residues to avoid formation of disulfide linkages between peptides, these substitutions are marked with underlining. The sequences for the resulting peptides are as follows: 1-35, (SEQ ID NO:22) GRDYRT SLTIVQKLKKMVDKPTQRSVSNAATRVSR; 36-70, (SEQ ID NO:23) TGRSRWRDV SRNFMRRYQSRVIQGLVAGETAQQIS; 1-20, (SEQ ID NO:24) GRDYRTSLTIVQKLKKMVDK; 31-50, (SEQ ID NO:11) TRVSRTGRSRWRDVSRNFMR; 16-35, (SEQ ID NO:25) KMVDKPTQRSVSNAATRVSR; 46-65, (SEQ ID NO:26) RNFMRRYQSRVIQGLVAGET; 61-80, (SEQ ID NO:27) VAGETAQQISEDLR. Additionally, the valine residue at position 44 of peptide 31-50 was substituted with a tryptophan, resulting in peptide 31-50v44w with the sequence of (SEQ ID NO:12) TRVSRTGRSRWRDW SRNFMR. Also, this same peptide sequence was synthesized with all D-type amino acids to generate peptide D-31-50v44w (SEQ ID NO:12) (TRVSRTGRSRWRDW SRNFMR) and with lauryl conjugation at the N-terminal end to generate peptide D-lauryl-31-50v44w. A shorter granulysin peptide with a substitution at position 45 with an alanine residue (SEQ ID NO:5) (RSRWRDVARNFMR) was also synthesized with and without a lauryl group resulting in peptides D-38-50s45a and D-lauryl-38-50s45a.

Granulysin peptide derivatives were assembled via solid phase peptide synthesis, using either an Applied Biosystems 433A or Symphony (Rainin/Protein Technologies, Inc.) automated peptide synthesizer at Ansata Therapeutics, Inc. Standard methods of Fmoc-based solid phase peptide synthesis were applied using modules in the software packages provided with the automated instrument. Rink amide resin and all amino acid derivatives (D- and L-) were purchased from EMD Biosciences/Novabiochem (San Diego, Calif.). Peptide couplings were achieved via activation as the HOBT ester using 2-(1H-benzotriazole-1-yl)-1,1,3,3-tetramethyluronium hexafluorophosphate (HBTU, American Bioanalytical, Natick, Mass.). Cleavage of the peptide from the solid phase resin was achieved with a cocktail consisting of 90% TFA and 2% each of water, triisopropylsilane, ethanedithiol, thioanisole, and phenol (all from Sigma-Aldrich, Milwaukee, Wis.) for 2.5 h. Crude peptides were purified to greater than 95% purity via $C_{18}$ reversed phase HPLC using acetonitrile-water-TFA eluant systems and lyophilized to dryness. Peptide identity was confirmed by MALDI-TOF mass spectrometry (Bruker Autoflex mass spectrometer, Bruker Daltonics, Inc.) in a matrix of α-cyanohydroxycinnamic acid (CHCA, Sigma-Aldrich). Amino acid analysis (Molecular Structure Facility at the University of California, Davis) was used to confirm peptide composition and content CFU assay. The CFU assay was performed as described previously (Ernst et al., (2000) Immunol 165:7102-7108). *Propionibacterium acnes* strain ATCC 6919 (American Type Cell Culture, Manassas, Va.) was grown under anaerobic conditions in Reinforced Clostridial Medium (Oxoid, Basingstroke, England) for two days and collected in mid-log phase. The bacteria were washed three times with the assay buffer, 10 mM sodium phosphate, pH 7.2, supplemented with 0.03% trypticase soy broth (TSB, Becton-Dickinson, Cockeysville, Md.), and enumerated by applying a conversion factor of $7.5 \times 10^7$ bacteria/mL=1 OD unit at 600 nm. Various concentrations of granulysin or granulysin peptides were incubated with $3.75 \times 10^5$ bacteria in a final volume of 30 μL at 37° C. for four hours. After incubation, 10-fold dilutions were prepared and plated on solid media comprised of *Brucella* broth (BD Biosciences, San Diego, Calif.) with 5% sheep red blood cells (Remel, Lenexa, Kans.), 0.5 mg/liter vitamin K, and 5.0 mg/liter hemin (Remel, Lenexa, Kans.). Plates were incubated for four days at 37° C. under anaerobic conditions, then individual colonies were counted and the number of CFU per tube was calculated.

Electron microscopy. *P. acnes* at a concentration of 2.08× $10^7$ bacteria/mL was suspended in 10 mM sodium phosphate buffer pH 7.2 supplemented with 0.03% TSB and incubated with 20 mM granulysin peptides. Samples were then fixed for 30 minutes with 2% gluteraldehyde in 1×PBS, pH=7.35, room temperature, then washed three times and suspended in 1 mL 1×PBS. Scanning EM samples were filtered onto a micropore filter. The filters with the sample on top were dehydrated in graded ethanol; 50, 75, 95 and 100%-15 minutes in each, followed by similar transfers in hexa-methyl-disilazane reagent; 50, 75, 95%-30 minutes each followed by 100% hexa-methyl-disilazane reagent overnight. The scanning EM samples were gold coated and then viewed and photographed on a Cambridge Scanning electron microscope. Transmission EM samples were dehydrated in graded ethanol as above, embedded in Epon, and sectioned on Sorvall MT6000 (RMC, Tucson Ariz.). Thin sections (75 μm) were stained with uranyl acetate, viewed and photographed on Jeol XC100 at 80-kV Primary Human Monocyte Isolation and Stimulation. Peripheral human blood was drawn from normal healthy volunteers into heparinized tubes according to a protocol approved by the Institutional Review Board at UCLA. PBMCs were then isolated on Ficoll-Paque gradients (Pharmacia, Piscataway, N.J.) and plated ($5 \times 10^5$/well) in 96-well plates for 2 hours in 1% FCS (Omega Scientific, Tarzana, Calif.). Non-adherent cells were removed by washing 3 times with RPMI media, leaving adherent cells. Adherent monocytes were cultured in 10% FCS with *P. acnes* sonicate, granulysin peptides, or *P. acnes* sonicate together with various concentrations of granulysin peptide for 24 hours at 37° C.

Monocyte supernatants were harvested and assayed for IL-12p40 using cytokine-specific, commercially available antibody pairs in a standard sandwich ELISA (Biosource International, Camarillo, Calif., or BD PharMingen, San Diego, Calif.). Capture antibodies were coated to 96-well EIA/RIA plates (Costar, Corning) and detection was achieved by incubating with biotinylated antibodies followed by Immunopure HRP-conjugated streptavidin (Pierce, Rockford, Ill.) and the ABTS Microwell Peroxidase Substrate System (Kirkegaard & Perry Laboratories, Gaithersburg, Md.). The absorbance at 405 nm was read using a microtiter plate reader, and cytokine concentrations were calculated from a standard curve of recombinant cytokine (Biosource or Pharmingen). Supernatants were assayed for other cytokines using Pierce SearchLight Multiplex Cytokine array services (Pierce Biotechnology, Woburn, Mass.).

Cell culture and viability assay. The human keratinocyte cell line, HaCaT, was cultured in DMEM (Gibco, Grand Island, N.Y.) supplemented with 10% fetal calf serum, penicillin at 10 U/mL, streptomycin at 10 U/mL, L-glutamine at 0.29 mg/mL, and sodium pyruvate at 1 μM. HaCaTs were grown to confluence in T-75 flasks (Corning, Corning, N.Y.), harvested by treatment with Trypsin-EDTA (Invitrogen, Carlsbad, Calif.), and seeded at $5 \times 10^3$ cells/well in a 96-well flat-bottom plate (Falcon, Becton Dickinson, Franklin Lakes, N.J.) for use in assays. Alternatively, peripheral blood mononuclear cells (PBMC) were isolated by Ficoll-Paque (Amersham Biosciences, Uppsala, Sweden) gradient and adhered to plates as described above.

The MTT assay previously described was used to determine the cytoxicity of granulysin and granulysin peptides against HaCaT cells and monocytes. Granulysin or granulysin peptides were diluted to various concentrations in tissue culture media and incubated with the adherent cells at 37° C. for 24 hours. Wells were then washed two times with 200 μL of 1×PBS, and incubated with 10 μl of 3-(4,5-Dimethyl-2-thiazolyl)-2,5-diphenyl-2H-tetrazolium bromide (MTT) (Sigma, St. Louis, Mo.) per 100 μL of the appropriate media in the absence of light at 37° C. After four hours, the reaction was stopped by the addition of 100 μL of 10% SDS, and incubated for an additional 8 hours at 37° C. The absorbance was then read at 570 nm with a SPECTRAmax Plus 384 multi-well plate reader (Molecular Devices, Sunnyvale, Calif.). Toxicity of granulysin and the granulysin-derived peptides was determined by comparing the $A_{570}$ to wells treated with various concentrations of $Na_2CrO_4$, which is toxic to the cells.

Results

Granulysin and granulysin peptides have antimicrobial activity against *P. acnes*. We hypothesized that antimicrobial proteins, having a broad spectrum of activity and being naturally present during acne, might be effective in combating *P. acnes*, a major therapeutic target in acne. One such protein is granulysin, which is localized in cytotoxic granules of NK and T cells and kills both gram positive and gram negative bacteria (Stenger et al., 1998). To determine whether the antimicrobial protein granulysin kills *P. acnes*, we tested the activity of recombinant human granulysin against *P. acnes* using the CFU assay. Granulysin exhibited antimicrobial activity in a dose-dependant manner, reducing the number of *P. acnes* CFU by approximately 4 logs at a concentration of 32 μM, while a control peptide derived from HSP70 had no effect (FIG. 1A).

The crystal structure of granulysin reveals that it contains five alpha helical domains, and the ability of granulysin to kill *Salmonella typhimurium* and *Escherichia coli* has been localized to regions of granulysin that include helices 2 or 3 (Anderson et al. (2003) J Mol Biol 325:355-365; Wang et al. (2000) J Immunol 165:1486-1490; Ernst et al., supra.) Therefore, we synthesized peptides based on the sequence of granulysin, some of which included these regions. Two peptides containing helix-loop-helix domains and corresponding to amino acid residues 1-35 and 31-50 were found to reduce the number of viable *P. acnes*; these peptides killed *P. acnes* in a dose dependent manner with 100 μM of peptide reducing the number of viable *P. acnes* by 2 and 4 logs, respectively (FIG. 1B). In contrast, four non-helix-loop-helix peptides (peptides 1-20, 16-35, 46-65, and 61-80) had little or no antimicrobial activity and reduced the number of viable *P. acnes* by <1 log(FIG. 1C). In whole, these data indicate that granulysin can kill *P. acnes*, and its antimicrobial activity can be localized to a smaller region of the molecule with a defined structural motif, the helix-loop-helix.

Figure 2:
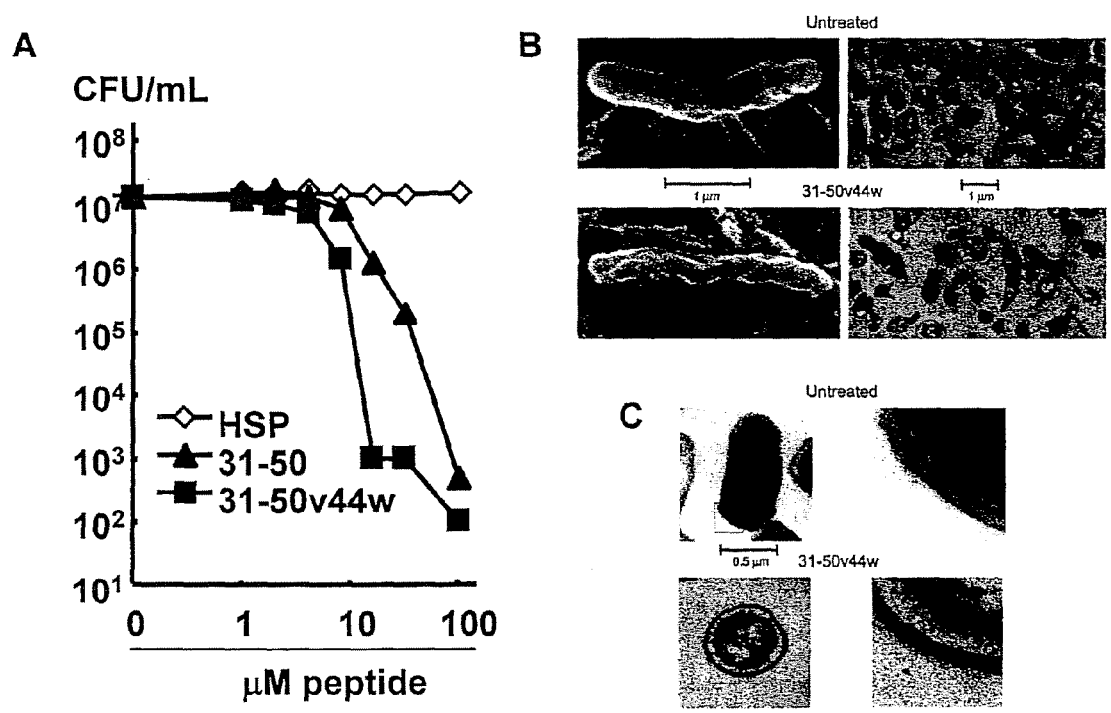
FIG. 2. Modification of granulysin peptide to enhance its antimicrobial activity. The antimicrobial effect of structure-function modification on granulysin peptide was determined. A hydrophobic residue, tryptophan, was added to the granulysin peptide 31-50 to create an anchor for the peptide in the bacterial surface. (A) Peptides 31-50 and 31-50v44w were then incubated with *P. acnes* and tested for antimicrobial activity by CFU assay. (B) SEM and low power TEM (10K magnification), demonstrated the effect of 31-50v44w on the surface of *P. acnes* was apparent after 72 hours as compared to the untreated control. (C) At higher power (36K magnification), peptide treatment was shown to disturb the sharply layered surface architecture of *P. acnes*, making the cell wall less distinct and more permeable to fluid influx.

Modification of a granulysin peptide enhances its antimicrobial activity. We next sought to determine whether modifications to peptide 31-50 could enhance its antimicrobial activity. As amino acid 44 resides in a scissor-like pocket between helices 2 and 3, we hypothesized that substitution at this position to create a hydrophobic anchor for the peptide in the bacterial surface would enhance killing. Our modeling indicated that substituting the valine at position 44 with a tryptophan (31-50v44w) would increase the Fauchere & Pliska hydrophobicity from −0.3 to 0.7. As a positive Fauchere & Pliska hydrophobicity correlates with strong antimicrobial activity, we predicted peptide 31-50v44w would have enhanced activity. We compared the antimicrobial activity of 31-50v44w to 31-50. Incubation with 32 μM of peptide 31-50v44w resulted in 2-3 logs fewer bacteria as compared to incubation with the peptide 31-50; the enhanced antimicrobial activity of 31-50v44w was evident over peptide concentrations ranging from 8-100CM and was dose-dependent (FIG. 2A). This demonstrates that modifications to increase peptide hydrophobicity may also increase the antimicrobial activity of the peptide.

Granulysin peptide 31-50v44w alters the surface of *P. acnes*. Granulysin exerts its antimicrobial activity against the Gram-negative bacterium *E. coli* by disturbing the integrity of the cell membrane. To determine if a similar mechanism is employed in the killing of *P. acnes*, a Gram-positive organism, by granulysin peptides, we examined bacteria that had been treated with 31-50v44w using both scanning EM and transmission EM. Both scanning and transmission EM micrographs of untreated *P. acnes* illustrate the bacterium's normal pleomorphic structure. By scanning EM, the surface of the untreated bacteria appeared smooth and rounded with fimbriae present while the peptide-treated bacteria demonstrated a recessed and withered surface with an absence of fimbriae (FIG. 2B). Similarly, differences between untreated and peptide-treated bacteria were appreciated by low magnification transmission EM which demonstrated many "ghost" cells after 72 hours of peptide treatment and few surviving bacteria with darker and more condensed cytoplasms compared to untreated bacteria. Higher magnification transmission EM revealed the untreated *P. acnes* had a cell wall with well-demarcated outer and inner dark, lipophilic layers and a lighter, hydrophilic peptidoglycan layer. In contrast, after only 1 hour of incubation with 31-50v44w, *P. acnes* lost the integrity of this surface architecture as the lighter, more hydrophilic, peptidoglycan layer as well as the darker more lipophilic layers of the cell wall appear disturbed, losing their crisp, well-defined structures (FIG. 2C). In addition, we observed a wider, likely edematous, space inside of the cell wall, further suggesting its disruption as well as peripheral clumping of nuclear material within the cell. In whole, these images reveal that peptide 31-50v44w perturbs the surface integrity of *P. acnes* in a manner that may make it porous, suggesting that this is the likely mechanism by which granulysin peptides kill this organism.

Figure 3:
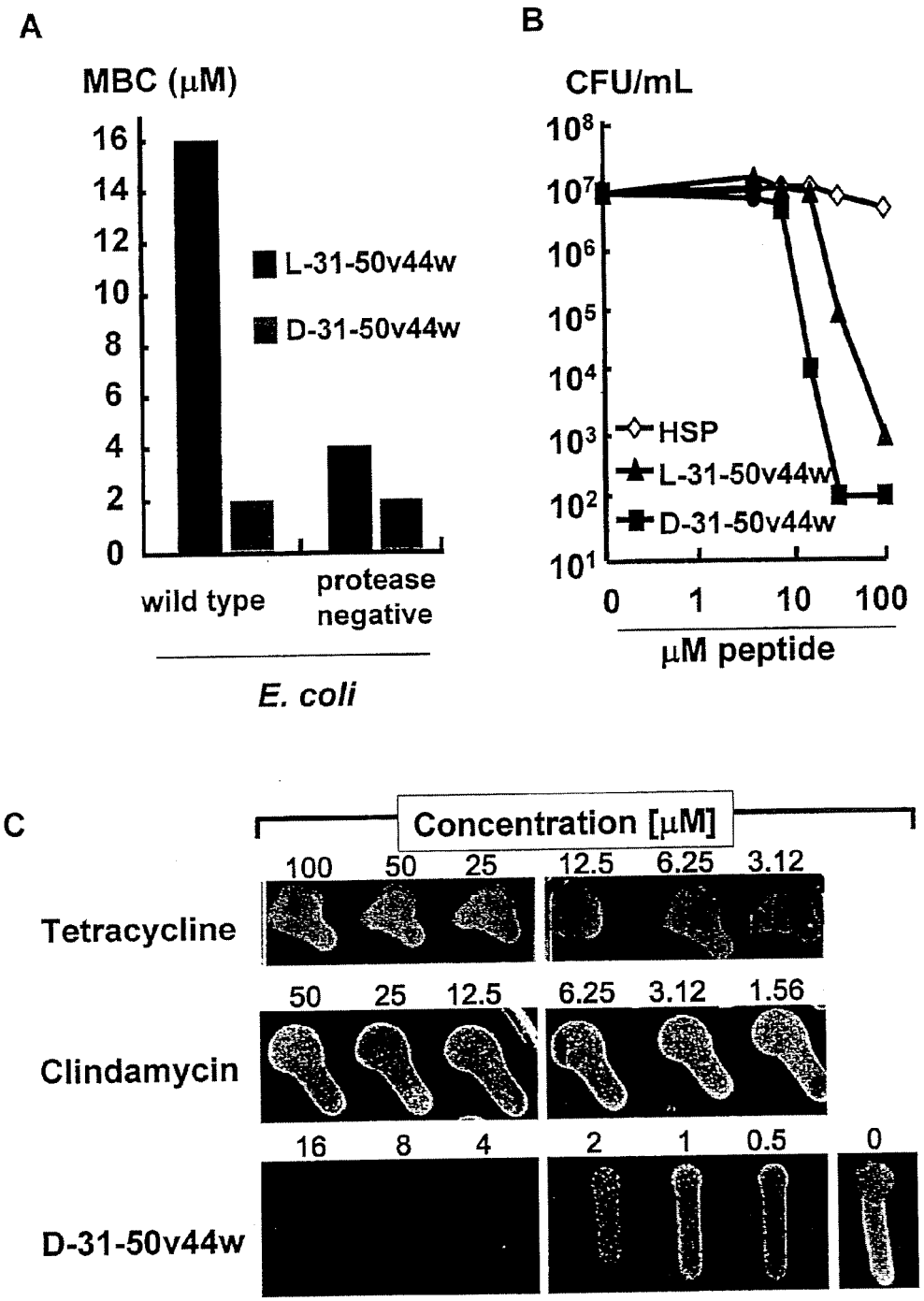
FIGS. 3A-C. Antimicrobial effects of granulysin peptides with D- and L-type amino acids. (A) Granulysin peptides with the sequence 31-50v44w were synthesized using only D-type amino acids (D-31-50v44w) or L-type amino acids (L-31-50v44w) and incubated with *P. acnes* and the antimicrobial activity was determined using CFU assay.

Further modification of 31-50v44w generates a peptide with greater antimicrobial activity. Since naturally occurring peptides exist in L-conformations and are susceptible to proteases, we synthesized a more stable peptide with the sequence 31-50v44w by using only D-type amino acids (D-31-50v44w) as they have been shown to be more protease-resistant. Granulysin peptides are superior antimicrobials compared to antibiotics currently used to treat acne. In comparing the antimicrobial activity of the granulysin peptides against that of widely used antibiotics, we found that tetracycline and clindamycin were bacteriostatic, preventing the further growth of *P. acnes*. On the other hand, peptide D-31-50v44w was bactericidal, capable of potently decreasing the number of viable *P. acnes* (FIG. 3C). Thus, granulysin peptides have an efficacy advantage over standard antibiotics in the control of *P. acnes*.

Figure 4:
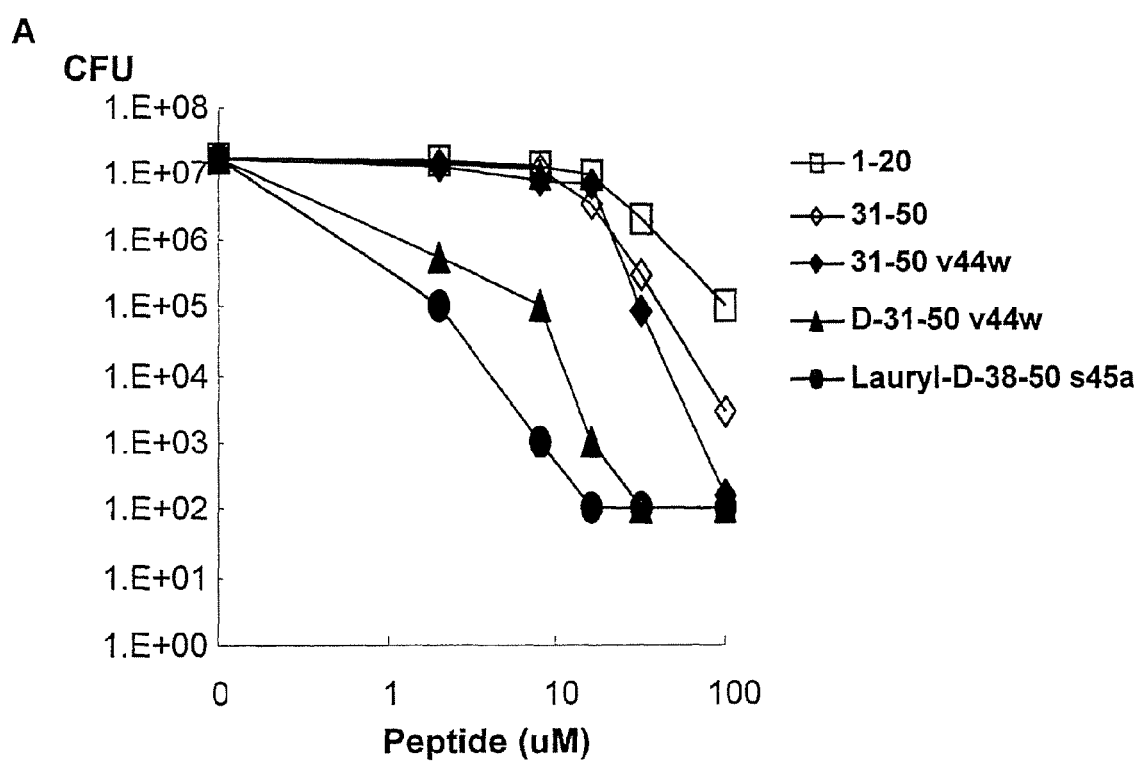
FIG. 4. Antimicrobial and Cytolytic Activity of Synthetic Granulysin Peptides (with Lauryl group). Various modified granulysin peptides (with lauryl group) were incubated with *P. acnes* at various concentrations for 4 hours, diluted in 10 mM NaPO$_4$ with 0.03% TBS and plated on TSB agar plates to determine antimicrobial activity by CFU assay (A). Various modified granulysin peptides (with lauryl group) were incubated with human monocytes (B) and human keratinocytes (C) and tested for cytolytic activity using MTT assay.
Figure 4:
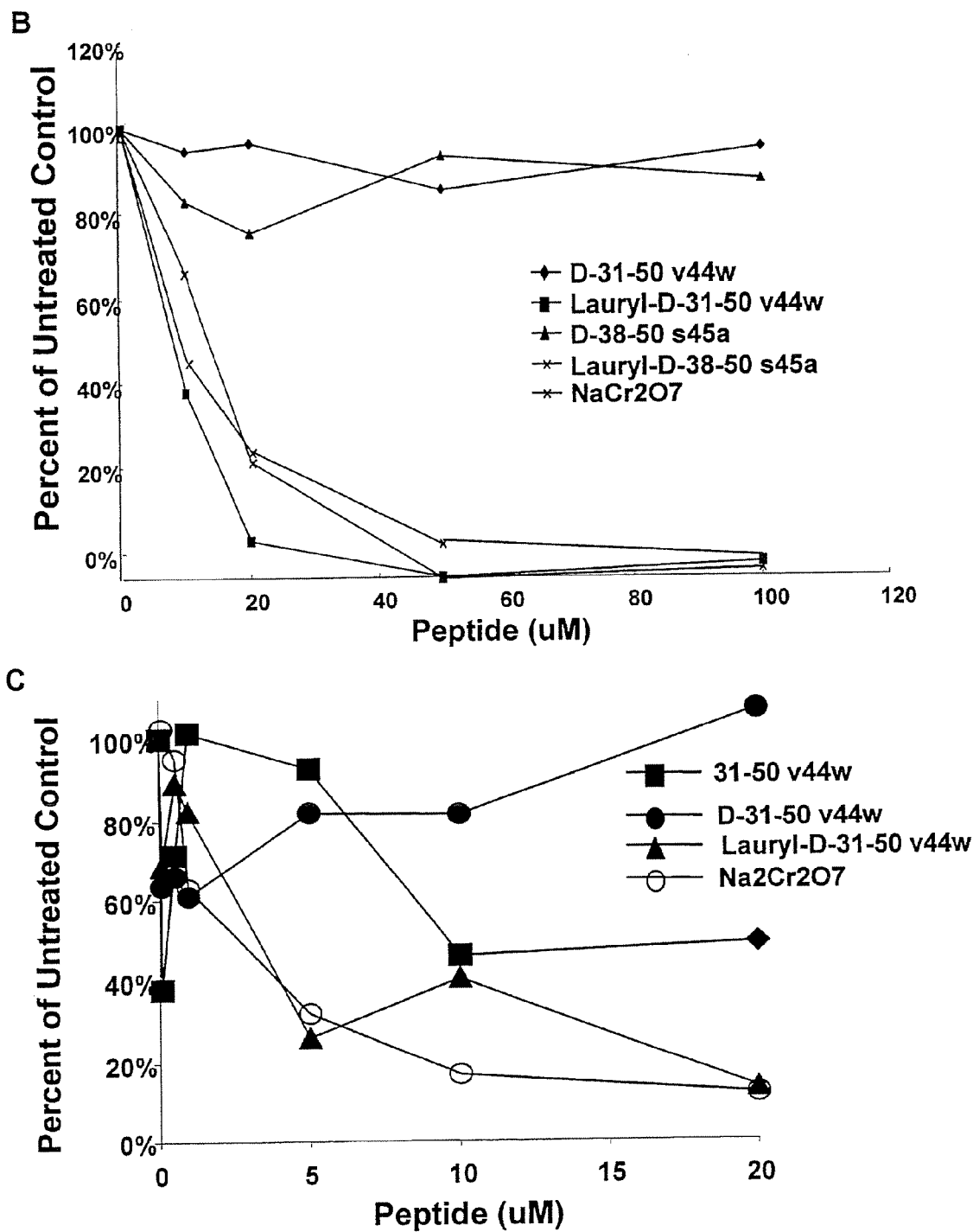

Addition of lipophilic lauryl group to granulysin peptides enhances antimicrobial activity against *P. acnes* and demonstrates cytolytic activity against eukaryotic cells. We made additional modifications to the granulysin peptide D-31-50v44w to enhance its antimicrobial activity. A lauryl group was added to the N-terminal end of the peptides. The modified peptide D-Lauryl-31-50v44w was more effective at killing *P. acnes* than similar peptides without the lauryl-conjugation (FIG. 4a). This finding was not specific to peptide D-31-50v44w. A shorter peptide with an alanine residue substitution at position 45, D-38-50s45a also showed more effective antimicrobial activity against *P. acnes* when a lauryl-group was conjugated to the peptide (D-lauryl-38-50s45a).

In addition, while the granulysin peptides without the lauryl group showed no cytolytic activity against human HaCaT keratinocytes cell line and primary human monocytes, the lauryl-conjugated granulysin peptides showed significant cytolytic activity against human keratinocytes and monocytes (FIG. 4b). These findings suggest that addition of lipophilic fatty acid moiety to enhance granulysin peptides' antimicrobial activity and cytolytic activity against eukaryotic cells are useful for treatment of acne. The cytolytic activity against human keratinocytes suggest that the granulysin peptides can be used as an exfoliative agent in acne. Furthermore, the cytolytic activity of granulysin peptides against transformed human keratinocytes cell line suggests that they can serve as an anti-tumor agent in the treatment of human skin cancers.

Anti-inflammatory effects of an antimicrobial granulysin peptide. An important component of acne is the inflammatory response elicited by *P. acnes*. Primary human monocytes stimulated with *P. acnes* secreted a wide variety of inflammatory cytokines and chemokines including IL-12p40, IL-12p70, IL-6, IL-8, MCP-1, IP-10, MIP-1a, MIP-3a, MDC, and ITAC. The production of these cytokines and chemokines may play important roles in the formation of inflammatory acne lesions. For instance, the induction of IL-8 by *P. acnes* may help recruit neutrophils to the skin, promoting pustule formation.

Figure 5:
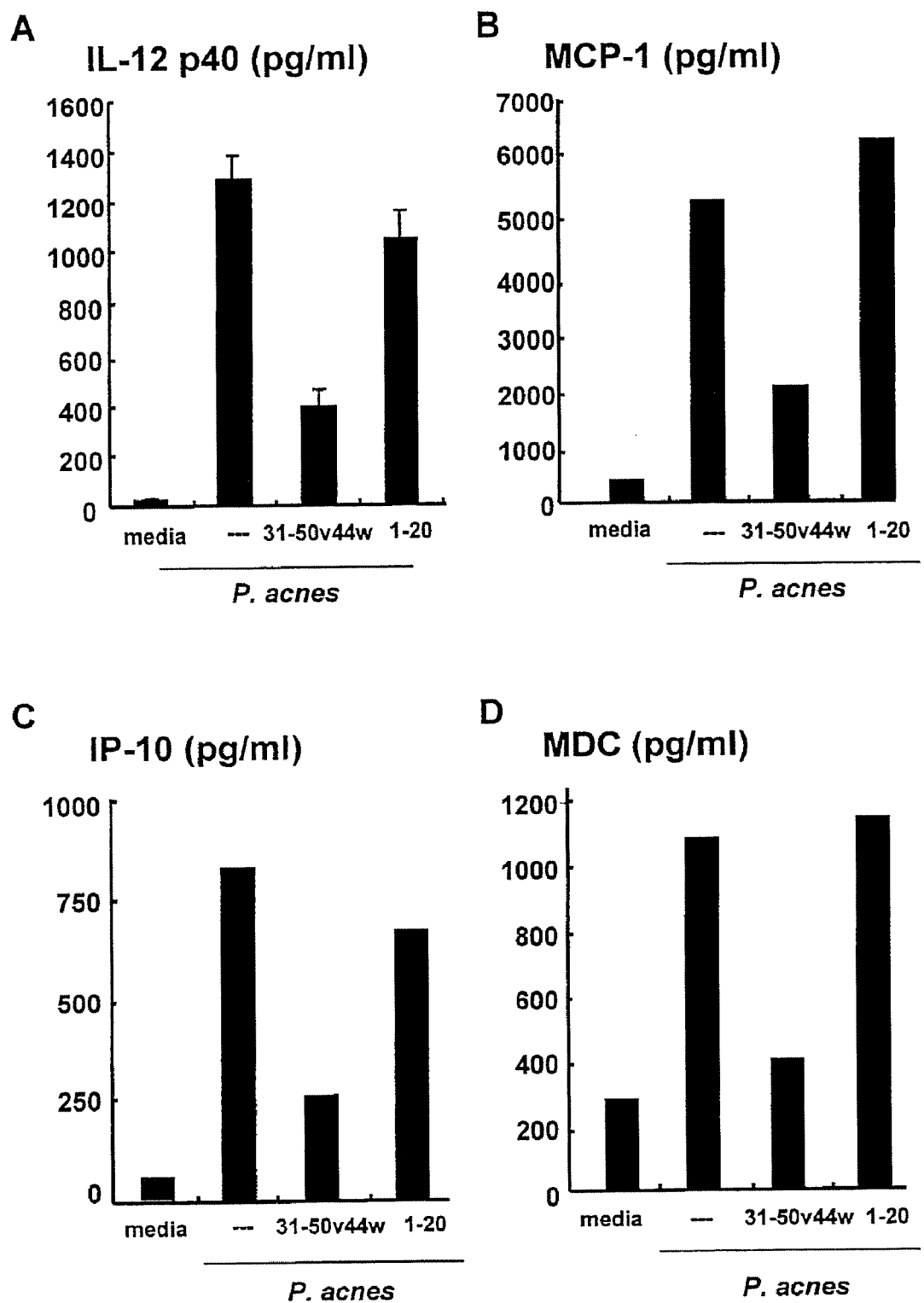
FIG. 5. The immunomodulatory effect of granulysin peptides. Granulysin peptide 31-50v44w was incubated with primary human monocytes which were subsequently stimulated with *P. acnes*. (A) IL-12p40 levels were determined by ELISA. The chemokines (B) MCP-1, (C) IP-10 and (D) MDC levels were determined by cytokine array (Pierce SearchLight Multiplex).

We determined whether peptide 31-50v44w could alter *P. acnes*-stimulated production of cytokines and chemokines from primary human monocytes. Importantly, 31-50v44w decreased *P. acnes*-stimulated production of IL-12p40, as compared to the non-helix-loop-helix peptides 1-20 and 16-35 (FIG. 5A). This decrease was determined to be statistically significant by the paired t-test (one-tail comparison $p=0.0037$, two-tail comparison $p=0.0074$). In addition, peptide 31-50v44w inhibited the production of several chemokines, including MCP-1, IP-10, and MDC, from *P. acnes*-stimulated monocytes (FIGS. 7B, 7C, 7D). Furthermore, granulysin peptide D-31-50v44w also decreased *P. acnes*-stimulated production of cytokines and chemokines (FIG. 5).

The increased incidence of drug resistance in clinical isolates of bacteria has underscored the need to identify new therapeutic agents. This issue is of particular importance in the treatment of *P. acnes*, a bacteria implicated in the pathogenesis of acne, since the increase in frequency of resistant strains is becoming a major clinical issue (Ross et al., 2003; Cooper, 1998; Coates et al., 2002). Since our immune system utilizes antimicrobial peptides to effectively combat infection, we hypothesized that these molecules may be suitable drug candidates. The ideal therapy for acne would be a potent antimicrobial agent with anti-inflammatory and keratolytic properties that maintains stability in and effectively penetrates the lipid-rich cutaneous environment. In this paper, we provide evidence that one such candidate, a modified granulysin peptide, effectively kills *P. acnes* in vitro. Moreover, our data demonstrate that in contrast to tetracycline and clindamycin, bacteriostatic agents currently used to treat acne, granulysin peptides are bactericidal. These peptides showed enhanced antimicrobial activity and cytolytic activity against eukaryotic cells with an addition of a lipophilic fatty acid moiety. Finally, these peptides demonstrate anti-inflammatory properties through their reduction of *P. acnes*-stimulated production of cytokines and chemokines. Furthermore, these peptides demonstrate keratolytic properties on human keratinocytes. The combined antimicrobial and anti-inflammatory activity of granulysin-derived peptides make them logical therapeutic agents for the treatment of acne. In addition, the cytolytic activity of granulysin peptides against human keratinocytes suggest that these peptides may also be useful as an exfoliative agent in the treatment of acne and as an anti-tumor agent in the treatment of skin cancers.

The secondary structure of an antimicrobial peptide has been shown to be essential for maintenance of its antimicrobial activity. Previous studies by Wang et al. demonstrated that peptides based on the sequence of granulysin that contained segments of either helix 2 (amino acids 23-36) or helix 3 (amino acids 42-51) were capable of lysing bacteria, identifying these regions as important for antimicrobial activity against *Salmonella typhimurium* (Wang et al., 2000). Furthermore, our earlier study demonstrated that peptides corresponding to amino acid residues 1-35, 31-50, and 36-70 which contain helix-loop-helix structures were capable of killing both *Escherichia coli* and *Mycobacterium tuberculosis*, while those peptides that did not contain this secondary structure were incapable of bacterial killing (Ernst et al., 2000). Similarly, here we provide evidence that granulysin peptides with helix-loop-helix structures, peptides 1-35 and 31-50, are effective at killing *P. acnes*. Additionally, it may be possible to design even shorter granulysin peptides with enhanced antimicrobial activity (Hamamoto et al., 2002).

An ideal topical antimicrobial therapy must be both potent in activity and stable to the cutaneous environment. We have modified the granulysin peptide 31-50 in three different ways to address these characteristics. First, we substituted the valine at amino acid position 44 for a tryptophan and created a peptide (31-50v44w) with enhanced antimicrobial activity against *P. acnes*. Since tryptophan residues have the ability to penetrate membranes, their presence in antimicrobial peptides has been correlated with antimicrobial activity (Fimland et al., 2002). For instance, NK-lysin, a member of the saposin-like protein family along with granulysin, has antimicrobial activity and has been shown to partially insert its tryptophan in membranes (Qi and Grabowski, 2001). Similarly, the native granulysin protein has one tryptophan at amino acid position 41 on helix 3, a highly lytic segment. Our EM studies document the ability of 31-50v44w to disrupt bacterial surface architecture. Although we do not show that there is a direct interaction between the tryptophan residues and the bacteria, the potent antimicrobial activity of this modified peptide suggests that tryptophans are indeed important for antimicrobial activity against *P. acnes*.

We next made an additional modification to granulysin peptide 31-50 to enhance its stability to proteases from both bacteria and human skin. We synthesized 31-50v44w entirely with D-type amino acids (D-31-50v44w) and found this peptide exhibited even greater potency in vitro as compared to 31-50v44w. Our experiments with *P. acnes* demonstrated that the D versus L form of 31-50v44w exhibited increased antimicrobial potency most likely due to its protease-resistance. This corroborates the findings of Alvarez-Bravo, et al. which found that the D-form of a sapecin B-derived peptide was able to avoid degradation by trypsin (Alvarez-Bravo et al., 1994). Further modification of the peptide with an addition of a lipophilic lauryl group enhanced antimicrobial activity and cytolytic activity against human cells, suggesting that our modified peptides may also be a useful exfoliative agent. Based on the enhanced activity and stability of these modified peptides, it is possible that additional modifications may even further improve their antimicrobial utility.

Antimicrobial peptides have been shown to have immunomodulatory functions. Here we show for the first time that granulysin peptides 31-50, 31-50v44w, and D-31-50v44w inhibit the production of inflammatory cytokines and chemokines by *P. acnes*-stimulated monocytes. *P. acnes* is a potent stimulator of host immune responses, and since inflammation is a key clinical feature of acne, the anti-inflammatory nature of these peptides increases their therapeutic potential. Previously, it has been shown that LL-37 decreases cytokine production in response to LPS, a Toll-like receptor 4 (TLR4) ligand (Scott et al., 2002). Here, we show that granulysin peptides decrease cytokine production in response to *P. acnes*, which stimulates cells through TLR2 (Kim et al., 2002). Although the precise anti-inflammatory mechanism is not known, it is possible that the peptides are interfering with aspects of the TLR2 pathway, such as the activation of NFκB. On the other hand, the peptide may be interacting with and binding up TLR ligands present in *P. acnes* sonicates, preventing some of these components from activating TLRs. Furthermore, since *P. acnes* contain a unique peptidoglycan, N-acetylmuramic acid-L-alanine-D-glutamate-L,L-diaminopimelic acid within the cell wall (Kamisango et al., 1982), it is possible that cytokine production may occur through the intracellular peptidoglycan receptors Nod1 or Nod2 which recognize similar motifs. Since *P. acnes* may contain ligands for Nods as well as TLRs, blocking of either of these pathways may explain the diminution of cytokine and chemokine production. Our current studies are exploring these potential mechanisms.

In this paper, we have demonstrated that an endogenous antimicrobial peptide, granulysin, can be a novel therapeutic agent in treating acne, one of the most common dermatologic conditions affecting over 85% of the population. The bactericidal and anti-inflammatory properties of granulysin peptides make them ideal candidates for the treatment of acne. Furthermore, we have demonstrated that modification of granulysin peptides can lead to more effective peptides that also has keratolytic activity against human keratinocytes. Whether granulysin peptides will be effective in clinical settings is not certain since there are no animal models for acne. Future clinical trials in humans will determine the outcome of their use. Certainly, the broad spectrum of activity increases the utility of granulysin peptides as they may be effective in treating other cutaneous infections caused by resistant bacteria.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for exfoliation of the skin of an individual, the method comprising:

applying to said skin a composition comprising a biologically active acylated granulysin peptide in a dose effective for topical cytolysis of keratinocytes and killing of *P. acnes*; and an acceptable vehicle, wherein the granulysin peptide has a sequence selected from:

SEQ ID NO:2 AATRVSRTGRSRWRDWSRNFMR;
SEQ ID NO:3 ERVSRTGRSRWRDWSRNFMRRR;
SEQ ID NO:4 RRVSRTGRSRWRDWSRNFMRRR;
SEQ ID NO:5 RSRWRDVARNFMR;
SEQ ID NO:6 RSRWRDVARNFMR; SEQ ID NO:7 RSRWRDWSRNFMR;
SEQ ID NO:8 RSVSNAATRVSRTGRSRWRDWSRNFMR;
SEQ ID NO:9 TRVARTGRSRWRDWARNFMR;
SEQ ID NO:10 TRVDRTGRSRWRDWZRNFMR;
SEQ ID NO:11 TRVSRTGRSRWRDVSRNFMR;
SEQ ID NO:12 TRVSRTGRSRWRDWSRNFMR;
SEQ ID NO:14 TRVSRTGRSRWRDWSRNFMRAA;
SEQ ID NO:15 TRVSRTGRSRWRDWSRNFMRAAKKKKKKKK;
SEQ ID NO:16 TRVSRTGRSRWRDWSRNFMRN;
SEQ ID NO:17 TRVSRTGRSRWRDWSRNFMRNW;
topical cytolysis SEQ ID NO:18 TRVSRTGRSRWRDWSRNFMRNY;
SEQ ID NO:19 TRVSRTGRSRWRDWSRNFMRRR;
SEQ ID NO:20 TRVSRTGRSRWRDWSRNWMRRR;
SEQ ID NO:21 TRVZRTGRSRWRDWDRNFMR.

2. The method of claim 1, wherein the peptide is (SEQ ID NO:12) TRVSRTGRSRWRDWSRNFMR or (SEQ ID NO:5) RSRWRDVARNFMR.

3. The method of claim 2, wherein the peptide is a D amino acid form.

4. The method of claim 1, wherein the acylated peptide comprises a lauryl group.

5. The method of claim 1, wherein said skin comprises acne lesions.

* * * * *